(12) United States Patent
Kitahara et al.

(10) Patent No.: US 6,489,430 B2
(45) Date of Patent: Dec. 3, 2002

(54) POLYISOCYANATE COMPOUNDS, PROCESS FOR PRODUCING THE SAME, AND OPTICAL MATERIALS USING THE SAME

(75) Inventors: Yoshitaka Kitahara, Tokyo (JP); Jian Jiang, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 09/931,053

(22) Filed: Aug. 17, 2001

(65) Prior Publication Data

US 2002/0103324 A1 Aug. 1, 2002

Related U.S. Application Data (62) Division of application No. 09/353,614, filed on Jul. 14, 1999, now Pat. No. 6,313,316.

(30) Foreign Application Priority Data

Jul. 14, 1998 (JP) ............................................. 10-198798
Jul. 14, 1998 (JP) ............................................. 10-198799

(51) Int. Cl.[7] ...................... C08G 18/77; C08G 18/74; C08G 18/28
(52) U.S. Cl. ............................................ 528/73; 528/85
(58) Field of Search ...................................... 528/73, 85

(56) References Cited

U.S. PATENT DOCUMENTS

| | | | | |
|---|---|---|---|---|
| 5,756,766 A | * | 5/1998 | Kawauchi et al. | ............. 549/22 |
| 6,313,316 B1 | * | 11/2001 | Kitahara et al. | ............... 549/22 |

FOREIGN PATENT DOCUMENTS

| | | | |
|---|---|---|---|
| EP | 0 435 306 | | 7/1991 |
| EP | 0 713 105 | | 5/1996 |
| EP | 972772 | * | 1/2000 |
| JP | 1-295201 | | 11/1989 |
| JP | 1-295202 | | 11/1989 |
| JP | 2-802 | | 1/1990 |
| JP | 02-153302 | | 6/1990 |
| JP | 4-159275 | | 6/1992 |
| JP | 5-105677 | | 4/1993 |
| JP | 06-065193 A | | 3/1994 |
| JP | 08-208801 A | | 8/1996 |
| JP | 08-269161 A | | 10/1996 |
| JP | 08-291210 A | | 11/1996 |
| JP | 08-291211 A | | 11/1996 |
| JP | 09-001565 A | | 1/1997 |
| JP | 09-071631 A | | 3/1997 |
| JP | 09-071632 A | | 3/1997 |
| JP | 10-045707 A | | 2/1998 |
| JP | 10-245429 A | | 9/1998 |

OTHER PUBLICATIONS

Patent Abstracts of Japan, 1–295201 A and JP 64–326636, "Resin for Material of Polyurethane Lens, Plastic Lens Comprising Polyurethane Resin and Production of the Lens," (Mitsui Toatsu Chem Inc., Nov. 28, 1989.

Patent Abstracts of Japan, 1–295202 A and JP 64–32639, "Resin for Material of Lens Comprising S–Alkyl Ester of Thiocarmabic Acid, Plastic Lens Comprising the Resin and Production of the Lens," Mitsui Toatsu Chem Inc., Nov. 28, 1989.

Patent Abstracts of Japan, 2–802 A and JP 64–32640, "High–Refractive Index Plastic Lens and Production Thereof," Mitsui Toatsu Chem Inc., Jan. 5, 1990.

Patent Abstracts of Japan, 2–153302 A and JP 64–32638, "Resin for High–Refractive Index Plastic Lens and Lens Consisting of This Resin and Production of the Lens," Mitsui Toatsu Chem Inc., Jun. 13, 1990.

Patent Abstracts of Japan, 4–159275 A and JP 2–281318, "Polyisocyanate Compound, Optical Material and Product Obtained by Using the Same," (Hoya Corp.), Jun. 2, 1992.

Patent Abstracts of Japan, 5–105677 A and JP 3–293632, "Polyisocyanate Compound, Optical Material and Optical Product Obtained By Using the Same," (Hoya Corp.), Apr. 27, 1993.

* cited by examiner

Primary Examiner—Rabon Sergent
(74) Attorney, Agent, or Firm—Morrison & Forester LLP (57) ABSTRACT

The invention provides a novel polyisocyanate compound which is useful as a starting material for an optical material having a high refractive index, a low dispersion and excellent optical characteristics, and a process for producing this compound at good efficiency. The invention also provides an optical material having a high refractive index, a low dispersion, an excellent transparency without optical distortion and having good heat resistance.

7 Claims, 4 Drawing Sheets

POLYISOCYANATE COMPOUNDS, PROCESS FOR PRODUCING THE SAME, AND OPTICAL MATERIALS USING THE SAME

This is a divisional application of U.S. application Ser. No. 09/353,614, filed Jul. 14, 1999 now U.S. Pat. No. 6,313,316.

This application is based on Japanese patent application Nos. H10-198798 and H10-198799, both filed on Jul. 14, 1998, the entire contents of which are incorporated herein by reference.

FIELD OF THE INVENTION

The invention relates to a polyisocyanate compound and a process for producing the same. In particular, it relates to a novel polyisocyanate compound useful as a starting material for an optical material, and a process for producing the same at good efficiency. It also relates to an optical material and an optical product using the same. Specifically, it relates to an optical material which has excellent optical characteristics such as a high refractive index, a low dispersion, an excellent transparency, lack of optical distortion and the like and good heat resistance, and to an optical product formed of this optical material, such as a lens, a prism, optical fibers, a substrate for a recording medium, a filter, a glass, a vase and the like.

BACKGROUND OF THE INVENTION

Recently, plastic materials have been used for optical parts in place of inorganic glass, especially for eyeglass lenses, because they are lightweight and have good dyeability and good impact resistance. In particular, a polyethylene glycol bisallylcarbonate polymer (hereinafter referred to as CR-39) and polymethyl methacrylate (PMMA) have been used, primarily for plastic lenses. However, it has a refractive index of 1.50, which is lower than that of inorganic glass. Therefore, when they are used as lens materials, for example, the thickness of the lenses has to be increased with the increasing power. Consequently, not only is the superiority of plastics as lightweight material been impaired, but also they have not been preferred in view of the aesthetic property. Furthermore, the concave lens, in particular, has had problems when the thickness (edge thickness) of the surrounding portion of the lens is increased causing a birefringence or a chromatic aberration to occur.

For these reasons, in order to be able to decrease the thickness of the lens while applying most of the characteristics of plastics having a low specific gravity, a plastic material having a high refractive index has been in demand. As a material having such a performance, for example, (1) a polymer comprising a xylene diisocyanate compound and a polythiol compound (official gazette of JP-A-63-46213), (2) a resin comprising an aliphatic linear sulfur-containing diisocyanate and a polythiol compound (official gazette of JP-A-2-153302), (3) a polymer comprising a dithian derivative substituted with two isocyanatoalkyl groups and a polythiol (official gazette of JP-A4-159275) are disclosed.

Although the resin in the above-mentioned item (1) and the resin in the above-mentioned item (2) have an increased refractive index by limiting a combination with a polythiol compound to be polymerized, the resin of item (1) has problems in that an Abbe number is decreased and a chromatic aberration is increased, and the resin of item (2) has a problem in that its heat resistance is decreased.

The polymer of item (3) has a high refractive index and a low dispersion (high Abbe number) and has an excellent heat resistance. However, in recent years, there has been a demand for a material having a higher refractive index and a lower dispersion.

SUMMARY OF THE INVENTION

In order to overcome many of the problems in the prior art, the invention provides an optical material having the above-mentioned desirable properties. It is a feature of the invention to provide a novel polyisocyanate compound which can give an optical material having a high refractive index, a low dispersion and an excellent heat resistance, and a process for producing this compound at good efficiency. It is also a feature of the invention to provide an optical material which has excellent optical characteristics such as a high refractive index, a low dispersion, an excellent transparency, lack of optical distortion and the like, and which has good heat resistance. It is also a feature of the invention to provide optical products made from the optical material.

In particular, the invention provides a polyisocyanate compound having a 1,4-dithian ring and an isocyanate group in a side chain connected by a sulfur atom. The compound exhibits a high refractive index, a low dispersion and high heat resistance. In addition, the invention provides methods for producing the polyisocyanate compound by an efficient processes. It also provides an optical material formed of a poly(thio)urethane obtained by subjecting a component comprising a polyisocyanate compound and a component comprising a compound having two or more of hydroxyl groups or mercapto or both groups to a polyaddition reaction.

In one aspect, the invention provides a polyisocyanate compound having general formula (I)

(I)

wherein X and Y independently represent an alkylene group having from 1 to 5 carbon atoms or an alkylene group having from 1 to 5 carbon atoms to which group an isocyanatoalkyl group is bound, wherein the carbon number of the alkyl group of the isocyanatoalkyl group is between 1 and 3 the alkylene groups optionally contain a sulfur atom, and m and n independently represent an integer from 1 to 3.

In another embodiment, the polyisocyanate compound can be produced by one of the following processes: production process 1 and production process 2.

Production process 1 of the invention is a process for producing a polyisocyanate compound represented by general formula (I-a)

(I-a)

wherein m and n, independently represent an integer from 1 to 3, $X^1$ and $Y^1$, independently represent an alkylene group having from 1 to 5 carbon atoms, and this alkylene group may have a sulfur atom.

Process 1 comprises:
(a) obtaining a dicarboxylic acid ester from a 2,5-bis (mercaptoalkyl)-1,4-dithian compound, said dicarboxylic acid being represented by general formula (III)

(III)

wherein $R^1$ and $R^2$, independently represent a lower alkyl group, $X^1$, $Y^1$, m and n are as defined above, said 2,5-bis(mercaptoalkyl)-1,4-dithian compound being represented by general formula (II)

(II)

wherein m and n are as defined above, (b) converting the dicarboxylic acid ester to a dicarbonyl hydrazide represented by general formula (IV)

(IV)

wherein m, n, $X^1$ and $Y^1$ are as defined above, and (c) converting the carbonyl hydrazide group into an isocyanate group.

Production process 2 of the invention is a process for producing a polyisocyanate compound represented by general formula (I-b)

(I-b)

wherein $A^1$ and $A^2$, independently represent a substituted alkylene group having from 1 to 5 carbon atoms, this alkylene group may have a sulfur atom, $B^1$ and $B^2$, independently represent an alkylene group having from 1 to 3 carbon atoms, m and n, independently represent an integer from 1 to 3, and k represents 0 or 1.

Process 2 comprises:

(a) obtaining a tricarboxylic acid ester or a tetracarboxylic acid ester from a 2,5-bis(mercaptoalkyl)-1,4-dithian compound, the tricarboxylic acid ester or the tetracarboxylic acid ester being represented by general formula (V)

(V)

wherein $A^1$, $A^2$, $B^1$, $B^2$, k, m and n are as defined above, and $R^3$ and $R^4$, independently represent a lower alkyl group, the 2,5-bis(mercaptoalkyl)-1,4-dithian compound being represented by the above-mentioned general formula (II), (b) converting the tricarboxylic acid ester or a tetracarboxylic acid ester to a tricarbonyl hydrazide or a tetracarbonyl hydrazide represented by general formula (VI)

(VI)

wherein $A^1$, $A^2$, $B^1$, $B^2$, m, n and k are as defined above, and (c) converting the carbonyl hydrazide group into an isocyanate group.

In another embodiment, the optical material of the invention is formed of a poly(thio)urethane comprising a polyisocyanate compound represented by general formula (I):

(I)

The polyisocyanate compound has an alicyclic structure. Preferably, the compound comprises isocyanatoalkyl groups having at least one sulfur atom and the groups are bound to the 2- and 5-positions of the 1,4-dithian ring.

In another aspect of the invention, in the above-mentioned general formula (I), X and Y, independently represent an alkylene group having from 1 to 5 carbon atoms or an alkylene group having from 1 to 5 carbon atoms to which group an isocyanatoalkyl group (in which the carbon number of the alkyl group is preferably between 1 to 3) is bound, and these alkylene groups may have a sulfur atom. It is preferable that the sulfur atoms are bound to two carbon atoms in the alkylene groups. The X and Y groups are independently a methylene group or an ethylene group, or a group represented by the formula:

(a)

(b)

or (c)

The groups are preferably: (a) a methylene group to which an isocyanatomethyl group is bound, (b) an ethylene group in which an isocyanatomethyl group is bound to a carbon atom bound to a sulfur atom or (c) an ethylene group in which an isocyanatomethyl group is bound to a carbon atom bound to an isocyanate group.

It is also preferred that m and n, independently represent an integer from 1 to 3.

It is preferred that the polyisocyanate compound represented by general formula (I) contains not only the 1,4-dithian ring but an additional sulfur atom outside the 1,4-dithian ring, preferably positioned to increase the refractive index and the Abbe number of the polyisocyanate compound. Accordingly, when an optical material is produced using this polyisocyanate compound, the refractive index and the Abbe number of the optical material are also increased.

Furthermore, it is preferred that the 1,4-dithian ring in the polyisocyanate compound is rigid. Therefore, when an optical material is produced using this, excellent mechanical characteristics can be given to the optical material.

Furthermore, it is preferred that in the polyisocyanate compound, when the isocyanatoalkyl groups (in which the carbon number of the alkyl group is preferably between 1 and 3) are bound to the alkylene groups having from 1 to 5 carbon atoms which groups may have a sulfur atom as indicated at X and Y in general formula (I), this compound itself becomes a crosslinking agent.

When an optical material is produced using the polyisocyanate compound, high heat resistance and a high solvent resistance can be imparted to the optical material without adding the other crosslinking agent as a secondary component.

BRIEF DESCRIPTION OF THE DRAWINGS

The invention will be better understood by reference to the Detailed Description of the Invention when taken together with the drawings, wherein.

DETAILED DESCRIPTION OF THE INVENTION

The process for producing the polyisocyanate compound represented by general formula (I) may be any process by which a polyisocyanate compound having a desired structure can be produced. However, it can be produced at quite good efficiency according to the processes 1 and 2 of the invention as mentioned below.

Production Process 1:

In this production process 1, first, a 2,5-bis(mercaptoalkyl)-1,4-dithian represented by general formula (II)

wherein m and n, independently represent an integer from 1 to 3, is used as a starting material. From this, a dicarboxylic acid ester represented by general formula (III)

wherein $R^1$ and $R^2$, independently represent a lower alkyl group, $X^1$ and $Y^1$, independently represent an alkylene group having from 1 to 5 carbon atoms, and this alkylene group may have a sulfur atom, and m and n are as defined above, is obtained.

To obtain this dicarboxylic acid ester represented by general formula (III), for example, it is preferable to use a method in which the 2,5-bis(mercaptoalkyl)-1,4-dithian represented by the above-mentioned general formula (II) is reacted with an aliphatic carboxylic acid lower alkyl ester having a halogen group such as a chlorine atom, a bromine atom or the like in the end in the presence of a hydrogen halide trapping agent, or a method in which it is reacted with an aliphatic carboxylic acid lower alkyl ester having a vinyl group in the end in the presence of a radical or anionic catalyst.

For example, when $X^1$ and $Y^1$ are each a methylene group in general formula (III), it is preferable to react the compound of formula (II) with a homohalogenoacetic acid lower alkyl ester. When $X^1$ and $Y^1$ are each an ethylene group, it is preferable to react the compound of formula (II) with an acrylic acid lower alkyl ester. And, when $X^1$ and $Y^1$ are the same, it is preferable to react 1 mol of the 2,5-bis(mercaptoalkyl)-1,4-dithian represented by general formula (II) with substantially 2 mols of an aliphatic carboxylic acid lower alkyl ester having a halogen group or a vinyl group in the end. Meanwhile, when $X^1$ and $Y^1$ are different, it is preferable to use a two-step method in which 1 mol of the 2,5-bis(mercaptoalkyl)-1,4-dithian represented by general formula (II) is first reacted with substantially 1 mol of an aliphatic carboxylic acid lower alkyl ester having a halogen group or a vinyl group in the end and then with substantially 1 mol of another aliphatic carboxylic acid lower alkyl ester having a halogen group or a vinyl group in the end.

In the above-mentioned reaction, an appropriate solvent can be used as required.

The dicarboxylic acid ester represented by general formula (III) is reacted with hydrazine monohydrate or the like to lead the same to a dicarbonyl hydrazide represented by general formula (IV)

(IV)

wherein m, n, $X^1$ and $Y^1$ are as defined above. At this time, a solvent such as a lower alcohol or the like can be used as required.

The dicarbonyl hydrazide represented by general formula (IV) can be reacted with nitrous acid in, for example, a hydrochloric acid aqueous solution, to form carbonyl azide and the heat transfer is conducted to convert a carbonyl azide group into an isocyanate group, whereby a desired polyisocyanate compound represented by general formula (I-a)

(I-a)

wherein m, n, $X^1$ and $Y^1$ are as defined above, is obtained.

Production Process 2:

In this production process 2, first, the 2,5-bis(mercaptoalkyl)-1,4-dithian represented by the above-mentioned general formula (II) is used as a starting material.

From the 2,5-bis(mercaptoalkyl)-1,4-dithian represented by the above-mentioned general formula (II), a tricarboxylic acid ester or a tetracarboxylic acid ester represented by general formula (V)

(V)

wherein $A^1$ and $A^2$, independently represent a substituted alkylene group having from 1 to 5 carbon atoms, this substituted alkylene group may have a sulfur atom, $R^3$ and $R^4$, independently represent a lower alkyl group, $B^1$ and $B^2$, independently represent an alkylene group having from 1 to 3 carbon atoms, k represents 0 or 1, and m and n are as defined above, is obtained.

To obtain the tetracarboxylic acid ester of the compounds represented by general formula (V), it is preferable to use a method in which the 2,5-bis(mercaptoalkyl)-1,4-dithian represented by the above-mentioned general formula (II) is reacted with an aliphatic dicarboxylic acid lower alkyl ester having a halogen group such as a chlorine atom, a bromine atom or the like in the molecule in the presence of a hydrogen halide trapping agent, a method in which it is reacted with an aliphatic carboxylic acid lower alkyl ester having a vinyl group in the molecule in the presence of a radical or anionic catalyst, or the like.

For example, when $A^1$ and $A^2$ are each a substituted ethylene group in which $B^1$ or $B^2$ is bound to a carbon atom bound to a sulfur atom and $B^1$ and $B^2$ are each a methylene group, it is preferable to react the same with a glutaconic acid di-lower alkyl ester (ROOC—$CH_2CH$=CH—COOR, R is a lower alkyl group). When $A^1$ and $A^2$ and $B^1$ and $B^2$ are the same respectively, it is preferable to react 1 mol of the 2,5-bis(mercaptoalkyl)-1,4-dithian represented by general formula (II) with substantially 2 mols of an aliphatic dicarboxylic acid lower alkyl ester having a halogen group or a vinyl group in the molecule. When $A^1$ and $A^2$ or $B^1$ and $B^2$ are each different, it is preferable to use a two-step method in which 1 mol of the 2,5-bis(mercaptoalkyl)-1,4-dithian represented by general formula (II) is first reacted with substantially 1 mol of an aliphatic dicarboxylic acid lower alkyl ester having a halogen group or a vinyl group in the molecule and then with substantially 1 mol of another aliphatic dicarboxylic acid lower alkyl ester having a halogen group or a vinyl group in the molecule.

To obtain the tricarboxylic acid ester (k=0) of the compounds represented by general formula (V), it is preferable to use a method in which 1 mol of the 2,5-bis(mercaptoalkyl)-1,4-dithian represented by the above-mentioned general formula (II) is first reacted with, as in the production method 1, substantially 1 mol of an aliphatic carboxylic acid lower alkyl ester having a halogen group or a vinyl group in the end and then with substantially 1 mol of an aliphatic dicarboxylic acid lower alkyl ester having a halogen group or a vinyl group in the molecule. Of course, it is also possible to conduct the reverse reaction.

In the above-mentioned reaction, an appropriate solvent can be used as required.

The tricarboxylic acid ester or tetracarboxylic acid ester represented by general formula (V) is reacted with hydrazine monohydrate or the like to lead the same to a tricarbonyl hydrazide or a tetracarbonyl hydrazide represented by general formula (VI)

(VI)

wherein $A^1$, $A^2$, $B^1$, $B^2$, m, n and k are as defined above. At this time, a solvent such as a lower alcohol or the like can be used as required.

Finally, the tricarbonyl hydrazide or tetracarbonyl hydrazide represented by general formula (VI) can be reacted with nitrous acid in, for example, a hydrochloric acid aqueous solution, and the heat transfer is conducted to convert a carbonyl hydrazide group into an isocyanate group, whereby a desired polyisocyanate compound represented by general formula (I-b)

(I-b)

wherein $A^1$, $A^2$, $B^1$, $B^2$, m, n and k are as defined above, is obtained.

The polyisocyanate compound represented by general formula (I) can also be produced by a phosgene method rather than the above-mentioned methods of the invention.

On phosgene method is described by example. First, 1 mol of the 2,5-bis(mercaptoalkyl)-1,4-dithian represented by general formula (II) is reacted with approximately 2 mols of chloroacetonitrile in the presence of a hydrogen chloride trapping agent to obtain a dinitrile represented by general formula (VII)

(VII)

wherein m and n are as defined above.

Then, the dinitrile is subjected to hydrogenation to lead it to a diamine represented by general formula (VIII)

(VIII)

wherein m and n are as defined above).

The compound is then reacted with phosgene to obtain a desired polyisocyanate compound represented by general formula (I-c)

(I-c)

wherein m and n are as defined above.

Examples of the polyisocyanate compound represented by general formula (I) in the invention, compounds having the following structures are the following:

-continued

Component (A) may contain, to appropriately improve properties and the like of the optical material, one or two or more types of a compound having two or more isocyanate groups in a molecule other than the polyisocyanate compound represented by the above-mentioned general formula (I). Specific examples of these compounds include o-xylene diisocyanate, m-xylene diisocyanate, p-xylene diisocyanate, α,α,α',α'-tetramethyl-p-xylylene diisocyanate, α,α,α',α'-tetramethyl-m-xylylene diisocyanate, 1,3,5-tris(isocyanatomethyl)benzene, hexamethylene diisocyanate, 1,4-diisocyanatobutane, isophorone diisocyanate, norbornene diisocyanate, bis(4,4'-isocyanatocyclohexyl)methane, 1,3-bis(isocyanatomethyl)cyclohexane, 1,3,5-tris(isocyanatomethyl)cyclohexane, 1,4-diisocyanatocyclohexane, 1,3,5-triisocyanatocyclohexane, lysine triisocyanate, 2,5-bis(isocyanatomethyl)-1,4-dithian, 1,3-dithiolan-4,5-diisocyanate, 4,5-bis(isocyanatomethyl)-1,3-dithiolan, isocyanatomethyl sulfide, 2-isocyanatoethyl sulfide, bis(isocyanatomethylthio)methane, 1,2-bis(isocyanatomethylthio)ethane, bis(2-isocyanatoethylthio)methane, 1,2-bis(2-isocyanatoethylthio)ethane, 1,7-diisocyanato-2,4,6-trithiaheptane, 1,5-diisocyanato-2-isocyanatomethyl-3-thiapentane, 1,4-diisocyanato-2-isocyanatomethyl-3-thiabutane and the like.

The content of the polyisocyanate compound represented by general formula (I) in component (A) is preferably 0.1 mol % or more, especially preferably 5 mol % or more.

Component (B), another starting material for the poly(thio)urethane, may contain a component comprising at least one type selected from (i) a compound having two or more mercapto groups in a molecule, (ii) a compound having two or more hydroxyl groups in a molecule and (iii) a compound having one or more hydroxyl groups and one or more mercapto groups in a molecule.

Examples of the compound having two or more mercapto groups in a molecule as the component (i) include 2,5-bis(mercaptomethyl)-1,4-dithian and its oligomer, 1,2,3-trimercaptopropane, tetrakis(7-mercapto-2,5-dithiaheptyl)methane, 1,2-ethanedithiol, 1,3-propanedithiol, tetrakismercaptomethylmethane, 2-mercaptoethyl sulfide, pentaerythritol tetrakismercaptopropionate, pentaerythritol tetrakismercaptoacetate, 1,2-benzenedithiol, 1,3-benzenedithiol, 1,4-benzenedithiol, 1,3,5-benzenetrithiol, 1,2-dimercaptomethylbenzene, 1,3-dimercaptomethylbenzene, 1,4-dimercaptomethylbenzene, 1,3,5-trimercaptomethylbenzene, toluene-3,4-dithiol, tris(3-mercaptopropyl) isocyanurate, 1,3-bis(mercaptomethyl)cyclohexane, 1,4-bis(mercaptomethyl)cyclohexane, 2,2-bis(mercaptomethyl)-1,3-propanediol, 1,2-bis(2-mercaptoethylthio)-3-mercaptopropane, 4,8-bis(mercaptomethyl)-3,6,9-trithia-1,11-undecanedithiol and the like.

Examples of the compound having two or more hydroxyl groups in a molecule as the component (ii) include ethylene glycol, trimethylolpropane, glycerin, dihydroxybenzene, catechol, 4,4'-dihydroxyphenyl sulfide, 2-hydroxyethyl sulfide, bisphenol A.propylene oxide 5-mol adduct, glycerin-propylene oxide 3-mol adduct and the like.

Examples of the compound having one or more hydroxyl groups and one or more mercapto groups in a molecule as the component (iii) include 2-mercaptoethanol, 2,3-dimercaptopropanol, 1,2-dihydroxy-3-mercaptopropane, 4-mercaptophenol and the like.

As a compound having two or more mercapto groups in the molecule, a mercapto group-containing compound is preferred. Especially, 2,5-bis(mercaptomethyl)-1,4-dithian and its oligomer represented by general formula (II-a)

(II-a)

wherein a is an integer from 1 to 20, is preferable.

With respect to the ratio of component (A) and component (B) in the invention, it is preferable that the molar ratio of the isocyanate group in component (A) to the total amount of the mercapto group and the hydroxyl group in component (B), NCO group/(SH group+OH group), is in the range of from 0.95 to 1.05.

The monomer mixture comprising component (A) and component (B) may contain one or two or more types of the compound having two or more vinyl groups in the molecule to appropriately improve the properties and the like of the optical material in addition to the components (A) and (B). With respect to the ratio of these compounds used at this time, it is preferable that the (isocyanate group+vinyl group)/(mercapto group+hydroxyl group) molar ratio is in the range of from 0.95 to 1.5 and the (vinyl group)/(isocyanate group) molar ratio is 0.7 or less, and that polymerizable functional groups contained in component (B) are all mercapto groups. Specific examples of these compounds include 2,5-bis(2-thia-3-butenyl)-1,4-dithian, divinylbenzene, ethylene glycol di(meth)acrylate, polyethylene glycol di(meth)acrylate, a urethane-modified (meth) acrylate comprising two or more (meth)acryloxy groups in a molecule and the like. By the way, the above-mentioned (meth)acrylate means both of an acrylate and a methacrylate, and the (meth)acryloxy group means both of an acryloxy group and a methacryloxy group.

To the optical material of the invention can be added an ultraviolet absorber, a coloring matter, a pigment and the like for improving light absorption characteristics, an antioxidant, a coloration inhibitor and the like for improving a weatherability, and a release agent and the like for improving a moldability, as required.

Examples of the ultraviolet absorber include a benzotriazole type, a benzophenone type, a salicylic acid type and the like. Examples of the coloring matter and the pigment include an anthraquinone type, an azo type and the like.

Examples of the antioxidant and the coloration inhibitor include a monophenol type, a bisphenol type, a high-molecular phenol type, a sulfur type, a phosphorus type and the like. Examples of the release agent include a fluorine-type surfactant, a silicone-type surfactant, an acidic phosphate, a higher fatty acid and the like.

A catalyst may be used, as required, to improve polymerization. For example, an amine compound, an organic metal compound and the like are effective. Specific examples thereof include triethylenediamine, hexamethylenetetramine, N,N-dimethyloctylamine, N,N,N', N'-tetramethyl-1,6-diaminohexane, 4,4'-trimethylenebis(1-methylpiperidine), 1,8-diazabicyclo-(5,4,0)-7-undecene, dimethyltin dichloride, dimethyltin bis(isooctylthioglycolate), dibutyltin dichloride, dibutyltin dilaurate, dibutyltin maleate, dibutyltin maleate polymer, dibutyltin diricinoleate, dibutyltin bis(dodecylmercaptide), dibutyltin bis(isooctylthioglycolate), dioctyltin dichloride, dioctyltin maleate, dioctyltin maleate polymer, dioctyltin bis(butylmaleate), dioctyltin dilaurate, dioctyltin diricinoleate, dioctyltin dioleate, dioctyltin di(6-hydroxy) caproate, dioctyltin bis(isooctylthioglycolate), didodecyltin diricinoleate, copper oleate, copper aceylacetonate, iron aceylacetonate, iron naphthenate, iron lactate, iron citrate, iron gluconate, potassium octanate, 2-ethylhexyl titanate and the like. The above-mentioned catalysts are effectively used either singly or in combination of two or more types.

When a vinyl compound is contained in the monomer mixture, the use of an organic peroxide, an azo compound or the like other than the catalyst is also effective.

An optical material using the polyisocyanate compound of the invention can be produced. The following is one example.

A uniform mixture of component (A), component (B), the additives and the catalyst is subjected to a known cast polymerization method. That is, it is cast into a die, which is a combination of a glass or metal mold and a gasket made of a resin, and cured by heating. In order to expedite withdrawal of the resin after molding, the mold may previously be subjected to release treatment, or a release agent may be added to the mixture of component (A), component (B) and the like. The polymerization temperature varies depending on the compound used. It is usually between −20 and +150° C. The polymerization time is typically between 0.5 and 72 hours. The optical material of the invention can easily be dyed in water or an organic solvent using an ordinary disperse dye. For further expediting the dyeing, a carrier may be added or heating may be conducted. The optical material is preferably used as a plastic lens, but is not limited thereto.

EXAMPLES

The invention is illustrated more specifically by referring to the following Examples. However, the invention is not intended to be limited to these Examples.

The properties of the polyisocyanate compounds and optical materials (polymers) were evaluated according to the following methods:

(1) $^1$H-NMR spectrum (proton nuclear magnetic resonance spectrum): Measured using an FT-NMR Device EX 270 Model supplied by JEOL.

(2) IR spectrum (infrared absorption spectrum): Measured using a MAGNA-IR Spectrometer 560 Model supplied by Nicolet.

(3) Refractive index ($n_D$) and Abbe number ($\alpha_D$): Measured at 20° C. using an Abbe refractometer 3T supplied by Atago.

(4) Appearance: Visually observed.

(5) Heat resistance: A dynamic viscoelasticity was measured with a static tension of 100 g and a frequency of 10 kHz by means of a dynamic viscoelasticity-measuring device supplied by Toyo Seiki Seisakusho. A heat resistance was evaluated in terms of a temperature of a decreasing point in a chart of a modulus of elasticity obtained at a rate of temperature rise of 2° C./min.

(6) Weatherability: A lens (optical product using an optical material) was mounted on a weather meter fitted with a sunshine carbon arc lamp. When 200 hours passed, the lens was taken out, and the color thereof was compared with that of the lens before the test. The weatherability was evaluated according to the following standard.

○: unchanged, Δ: slightly yellowed, ×: yellowed (7) Optical distortion

Visually observed by the Schlieren method. The optical distortion was evaluated according to the following standard.

○: No distortion is observed, ×: Distortion is observed.

Example 1

Production of 2,5-bis(4-isocyanato-2-thiabutyl)-1,4-dithian 31.8 g of 2,5-bis(mercaptomethyl)-1,4-dithian (0.15 mols) and 25.8 g (0.3 mols) of methyl acrylate were dissolved in 150 ml of chloroform. Triton B (40% by weight methanol solution, 0.8 g) was added as a catalyst in an ice bath, and the solution was stirred under reflux for 3 hours. The reaction solution was allowed to cool, then washed with a dilute sodium hydroxide aqueous solution and with water in this order, and dried over magnesium sulfate. Thereafter, chloroform was fully removed to obtain 46.8 g (0.12 mols) of a colorless transparent ester compound.

The ester compound was dissolved in 100 ml of methanol, and added dropwise to a mixed solution of 36.0 g (0.72 mols) of hydrazine hydrate and 36 ml of methanol at room temperature. After the completion of the dropwise addition, the mixture was stirred at 70° C. for 4 hours. Since white crystals were precipitated while the mixture was allowed to cool, these were collected through filtration, and recrystallized from methanol-water to obtain 39.3 g (0.11 mols) of a hydrazide compound.

The hydrazide compound was dissolved in 160 g of a 7.2% by weight hydrochloric acid aqueous solution, and 16.7 g (0.24 mols) of sodium nitrite were added to a suspension with 100 ml of chloroform. After the completion of the addition, the stirring was continued for 1 hour. The organic phase was withdrawn from the suspension, washed with water, dried (magnesium sulfate), and then heated to complete the transition reaction. Chloroform was filly removed from the reaction solution to obtain 22.1 g (0.063 mols) of a colorless transparent reaction product. This reaction product was identified to be desired 2,5-bis(4-isocyanato-2-thiabutyl)-1,4-dithian from the $^1$H-NMR spectrum and the IR spectrum.

Figure 1:
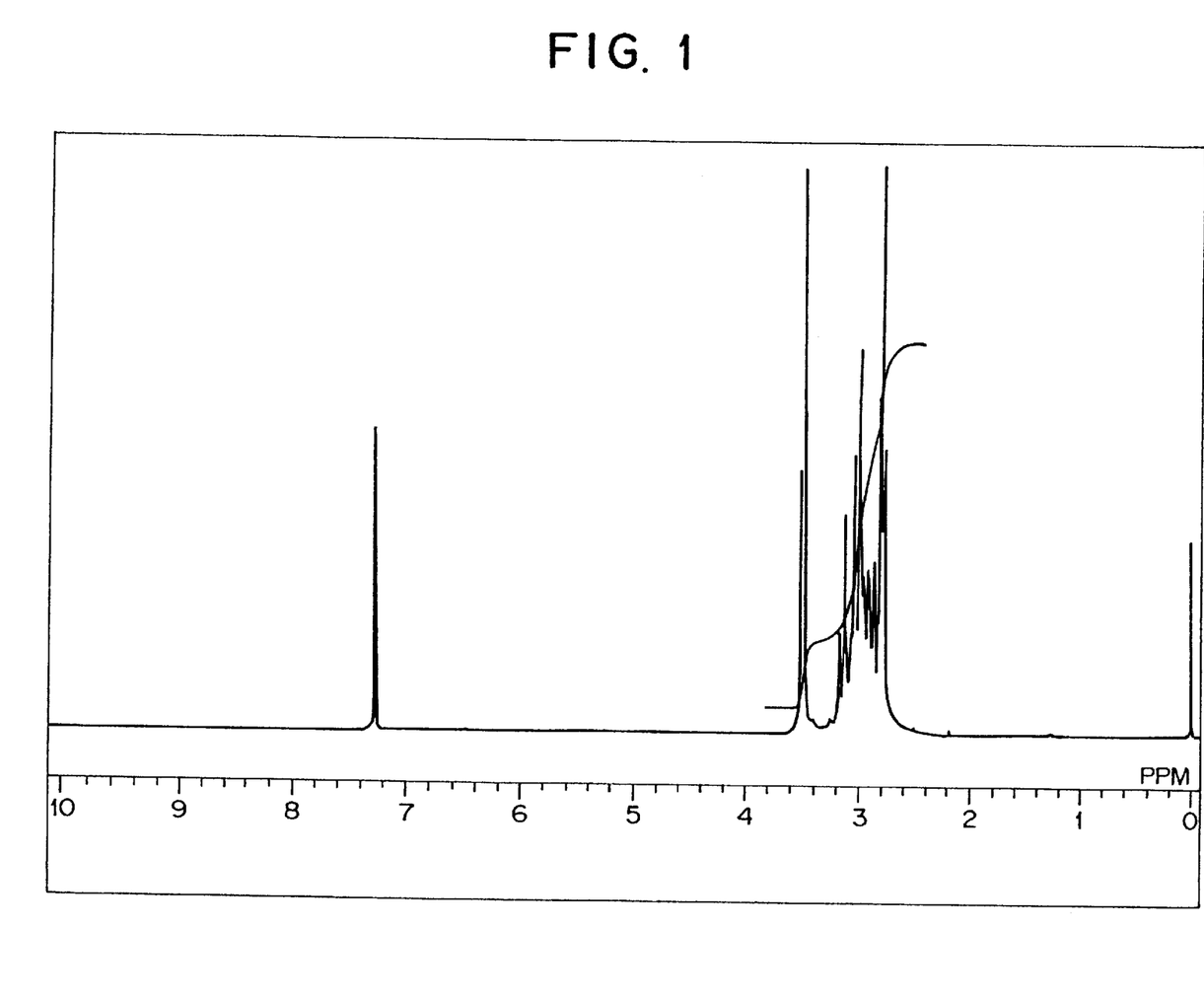
FIG. 1 shows a $^1$H-NMR spectrum of 2,5-bis(4-isocyanato-2-thiabutyl)-1,4-dithian obtained in Example 1.
Figure 2:
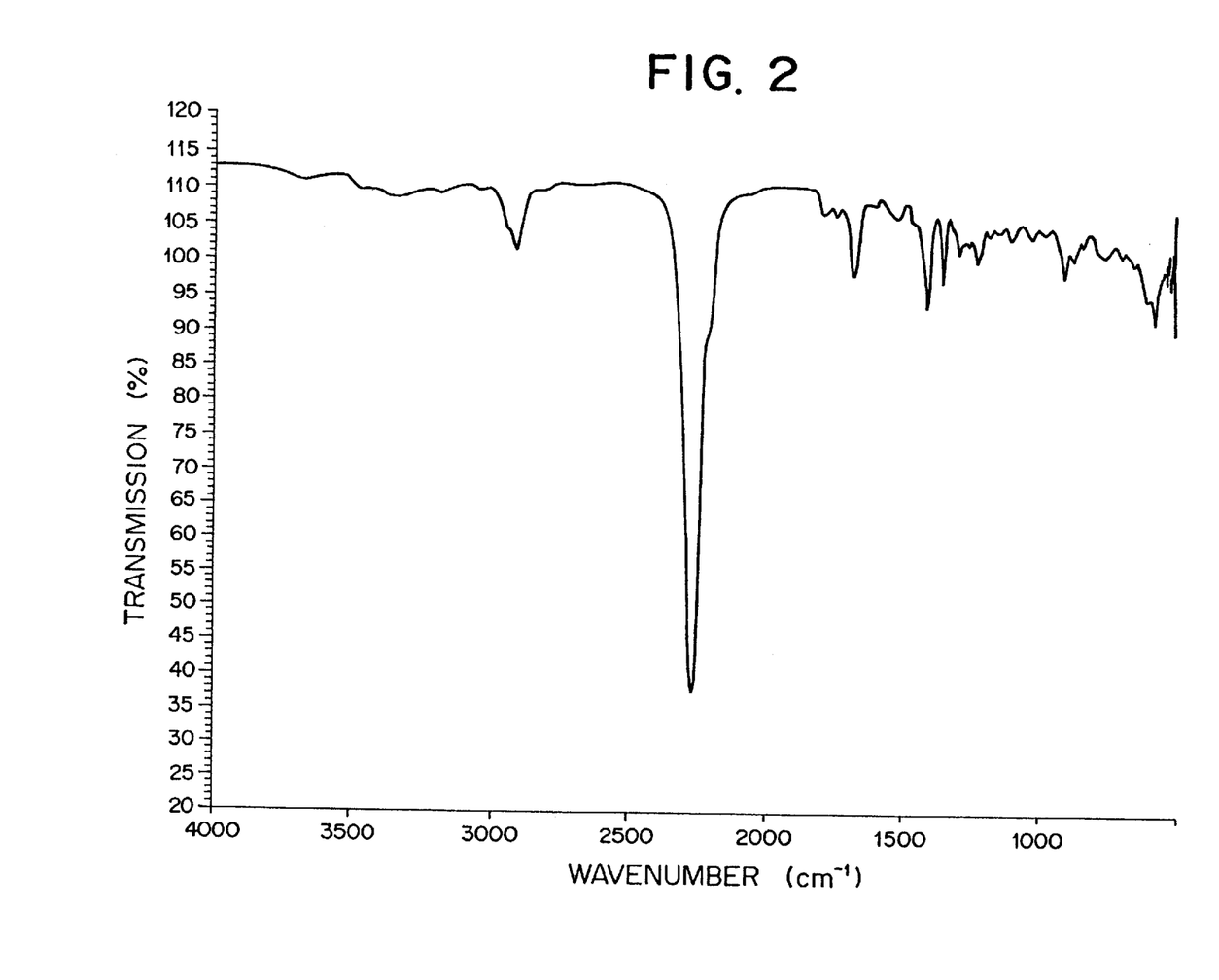
FIG. 2 shows an IR spectrum of 2,5-bis(4-isocyanato-2-thiabutyl)-1,4-dithian obtained in Example 1.

The $^1$H-NMR spectrum of the polyisocyanate compound is shown in FIG. 1, and the IR spectrum thereof in FIG. 2.

Example 2

Production of 2,5-bis(3-isocyanatomethyl-4-isocyanato-2-thiabutyl)-1,4-dithian 26.5 g of 2,5-bis(mercaptomethyl)-1,4-dithian (0.125 mols) and 46.6 g (0.25 mols) of diethyl glutaconate were dissolved in 100 ml of tetrahydrofuran. 0.65 g of tetrabutylammonium fluoride (0.0025 mols) was added as a catalyst in an ice bath, and the solution was stirred under reflux for 2 hours. The reaction solution was allowed to cool, and tetrahydrofuran was then removed. Benzene (150 ml) was added to the residue. The mixture was washed with a dilute sodium hydroxide aqueous solution and with water in this order, and dried over magnesium sulfate. Thereafter, benzene was fully removed to obtain 61.4 g (0.105 mols) of a pale yellow transparent ester compound.

The ester compound was dissolved in 26 ml of methanol, and added dropwise to a mixed solution of 104.2 g (2.08 mols) of hydrazine monohydrate and 26 ml of methanol at room temperature. After the completion of the dropwise addition, the mixture was stirred at 80° C. for 4 hours. The reaction solution was allowed to cool, and then added to 300 ml of methanol. A yellow solid precipitated was collected through filtration, and washed with hot ethanol-water to obtain 21.9 g (0.042 mols) of a hydrazide compound.

The hydrazide compound was dissolved in 600 g of a 15% by weight hydrochloric acid aqueous solution, and 12.6 g (0.18 mols) of sodium nitrite were added to a suspension with 300 ml of toluene. After the completion of the addition, the stirring was continued for 1 hour. The organic phase was extracted from the suspension, washed with water, dried (magnesium sulfate), and then heated to complete the transition reaction. Toluene as a solvent was fully removed from the reaction solution to obtain 6.6 g (0.014 mols) of a colorless transparent reaction product. This reaction product was identified to be desired 2,5-bis(3-isocyanatomethyl-4-isocyanato-2-thiabutyl)-1,4-dithian from the $^1$H-NMR spectrum and the IR spectrum.

Figure 3:
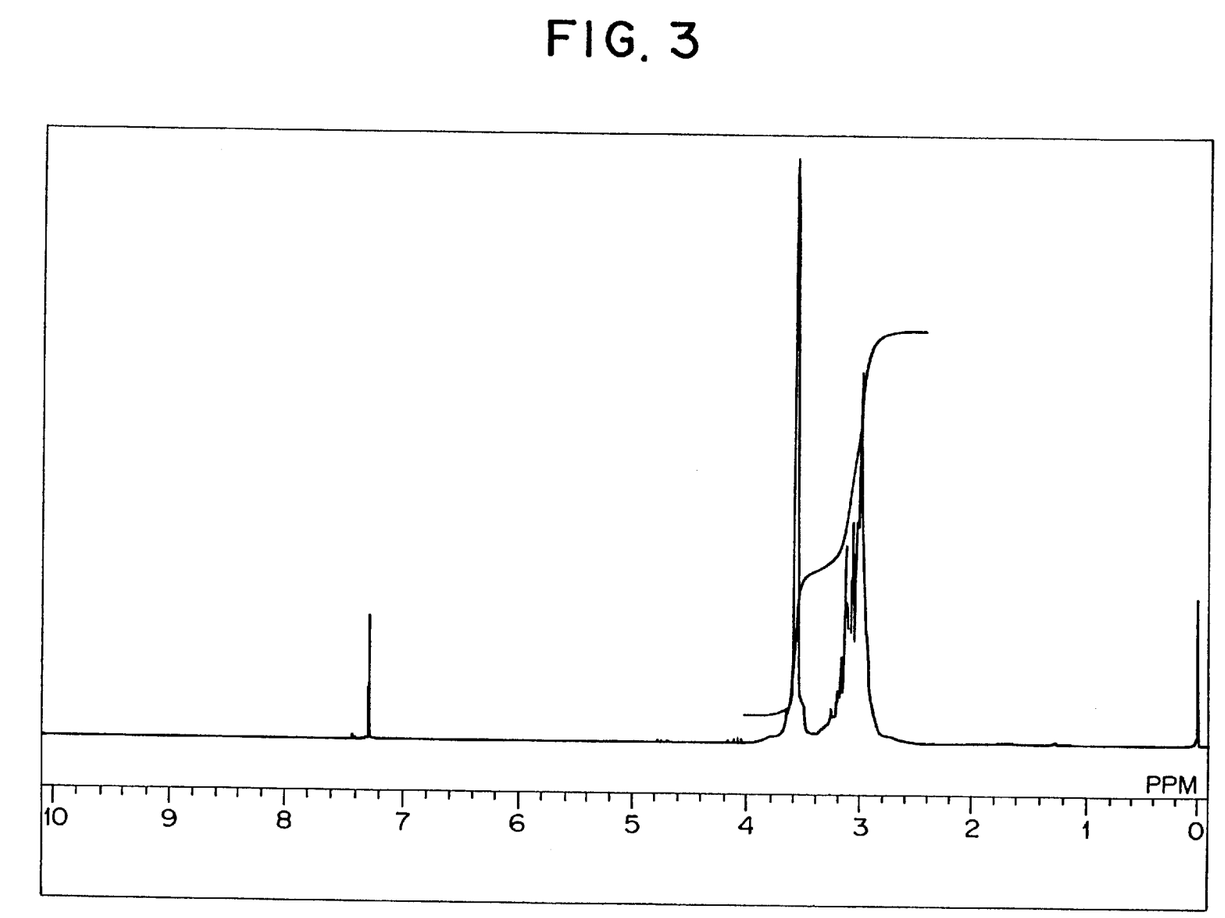
FIG. 3 shows a $^1$H-NMR spectrum of 2,5-bis(4-isocyanatomethyl-4-isocyanato-2-thiabutyl)-1,4-dithian obtained in Example 2.
Figure 4:
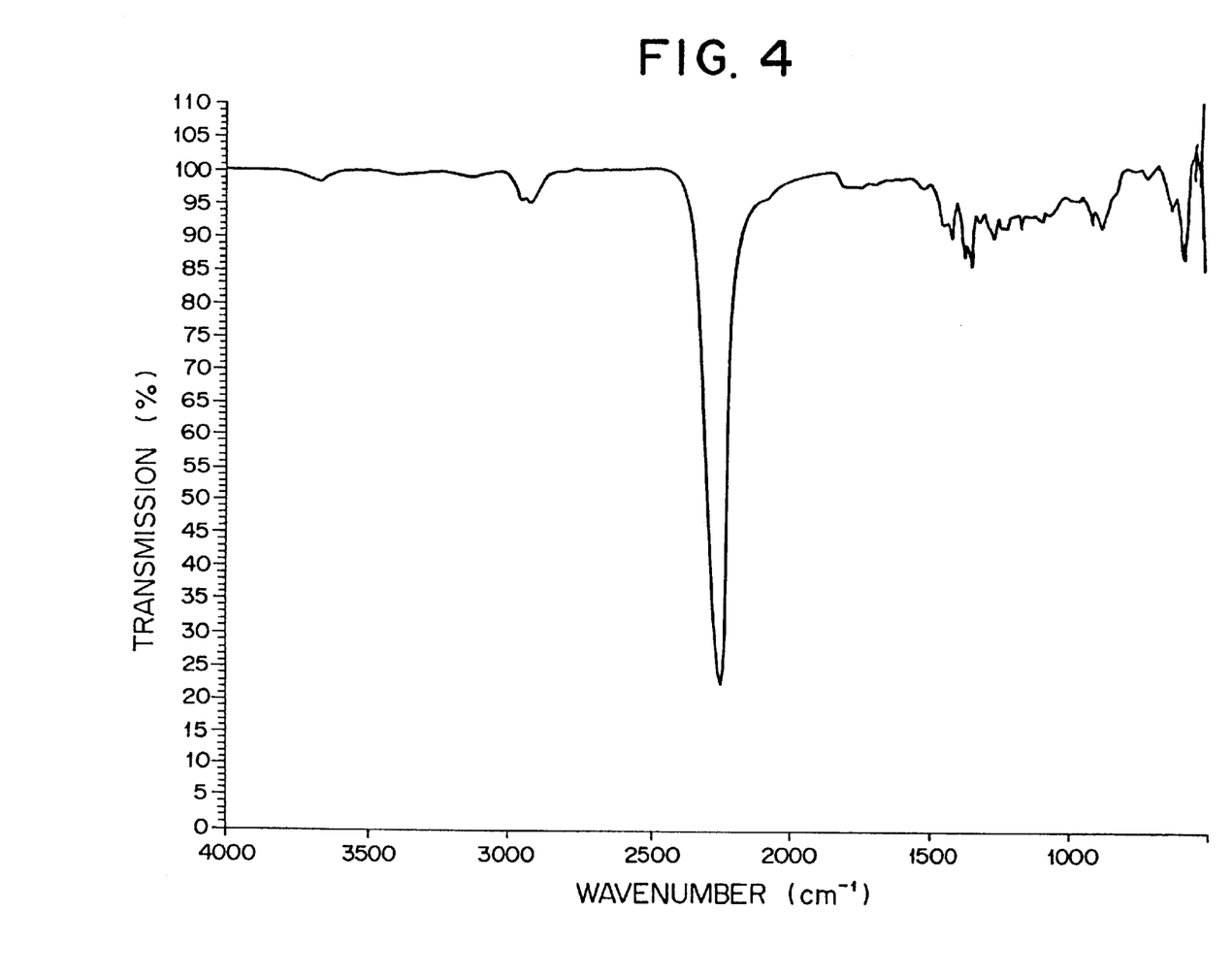
FIG. 4 shows an IR spectrum of 2,5-bis(3-isocyanatomethyl-4-isocyanato-2-thiabutyl)-1,4-dithian obtained in Example 2.

The $^1$H-NMR spectrum of the polyisocyanate compound is shown in FIG. 3, and the IR spectrum thereof in FIG. 4.

Application Example 1

A mixture of 0.10 mols of 2,5-bis(4-isocyanato-2-thiabutyl)-1,4-dithian (designated DT-1 in Table 1) obtained in Example 1, 0.10 mols of 2,5-bis(mercaptomethyl)-1,4-dithian (designated DMMD in Table 1) and $1.0 \times 10^4$ mols of dibutyltin dilaurate (designated DBTDL in Table 1) was uniformly stirred, and cast into two glass molds for forming a lens. The mixture was heat-polymerized at 50° C. for 10 hours, then at 60° C. for 5 hours and further at 120° C. for 3 hours to obtain a plastic lens. The properties of the resulting plastic lens are shown in Table 1. From Table 1, it was found that the polymer obtained by using the polyisocyanate compound of Example 1 was colorless and transparent, the refractive index (nD) was as high as 1.67, the Abbe number ($\alpha_D$) was also as high as 36 (low dispersion), the weatherability and the heat resistance (114° C.) were excellent, and no optical distortion was observed.

Application Example 2

A mixture of 0.06 mols of 2,5-bis(3-isocyanatomethyl-4-isocyanato-2-thiabutyl)-1,4-dithian (designated DT-2 in Table 1) obtained in Example 2, 0.12 mols of DMMD and $1.2 \times 10^{-4}$ mols of dibutyltin dilaurate (designated DBTDL in Table 1) was uniformly stirred, and cast into two glass molds for forming a lens. The mixture was polymerized at 50° C. for 10 hours, then at 60° C. for 5 hours and further at 120° C. for 3 hours to obtain a plastic lens. The properties of the resulting plastic lens are shown in Table 1. From Table 1, it was found that the polymer obtained by using the polyisocyanate compound of Example 2 was colorless and transparent, the refractive index (nD) was as high as 1.67, the Abbe number (VD) was also as high as 37 (low dispersion), the weatherability and the heat resistance (127° C.) were excellent, and no optical distortion was observed.

Application Examples 3 to 11

The same procedure as in Application Example 1 was conducted except using a monomer composition comprising each of the polyisocyanate compounds DT-1 and DT-2, i.e., 2,5-bis(4-isocyanato-2-thiabutyl)-1,4-dithian and 2,5-bis(3-isocyanatomethyl-4-isocyanato-2-thiabutyl)-1,4-dithian, respectively, obtained in Examples 1 and 2 and 2,5-bis(3-isocyanato-2-thiapropyl)-1,4-dithian (designated DT-3 in Table 1) as shown in Table 1 to obtain a plastic lens. The properties of these plastic lenses were shown in Table 1. From Table 1, it was found that the resulting plastic lenses were colorless and transparent, the refractive index (nD) was as high as between 1.65 and 1.69, the Abbe number (VD) was also as high as between 35 and 38 (low dispersion), the heat resistance (96 to 127° C.) and the weatherability were excellent, and no optical distortion was observed.

Application Comparative Example 1

A mixture of 0.06 mols of pentaerythritol tetrakismercaptopropionate (designated PETMP in Table 1), 0.12 mols of m-xylene diisocyanate (designated XDI in Table 1) and $1.2 \times 10^{-4}$ mols of dibutyltin dilaurate (designated DBTDL in Table 1) was uniformly stirred, and cast into two glass molds for forming a lens. The mixture was heat-polymerized at 50° C. for 10 hours, then at 60° C. for 5 hours and further at 120° C. for 3 hours to obtain a plastic lens. The properties of the resulting plastic lens are shown in Table 1. From Table 1, it was found that the plastic lens in this Application Comparative Example 1 was colorless and transparent, and no optical distortion was observed, but the refractive index was as poor as 1.59.

Application Comparative Examples 2 and 3

The same procedure as in Application Comparative Example 1 was conducted except using monomer compositions shown in Table 1 to obtain plastic lenses. The properties of these plastic lenses were shown in Table 1. From Table 1, it was found that the plastic lens in this Application Comparative Example 2 had a high refractive index of 1.68 and was excellent in the heat resistance (128° C.). However, it was colored yellow, the Abbe number was low (25), the weatherability was poor, and the optical distortion was observed. Further, the plastic lens in this Application Comparative Example 3 was colorless and transparent, and had a high refractive index of 1.66. However, the optical distortion was observed, and the heat resistance (71° C.) was also poor.

TABLE 1

| | | Component (A) (mol) | Component (B) (mol) | Catalyst (mol) | $n_D/v_D$ | Appearance | Heat Resistance (° C.) | Weatherability | Optical distortion |
|---|---|---|---|---|---|---|---|---|---|
| Application Example | 1 | DT-1 (0.10) | DMMD (0.10) | DBTDL ($1.0 \times 10^{-4}$) | 1.67/36 | colorless, transparent | 114 | ○ | ○ |
| | 2 | DT-2 (0.06) | DMMD (0.12) | DBTDL ($1.2 \times 10^{-4}$) | 1.67/36 | colorless, transparent | 127 | ○ | ○ |
| | 3 | DT-1 (0.12) | PETMP (0.06) | DBTDL ($1.2 \times 10^{-4}$) | 1.65/39 | colorless, transparent | 102 | ○ | ○ |
| | 4 | DT-1 (0.12) | KSD (0.09) TMP (0.02) | DBTDC ($1.2 \times 10^{-4}$) | 1.68/36 | colorless, transparent | 98 | ○ | ○ |
| | 5 | DT-1 (0.09) CHTI (0.02) | KSD (0.12) | DBTDC ($1.2 \times 10^{-4}$) | 1.66/37 | colorless, transparent | 109 | ○ | ○ |
| | 6 | DT-1 (0.085) HMTI (0.03) | KSD (0.13) | DBTDL ($1.3 \times 10^{-4}$) | 1.65/38 | colorless, transparent | 110 | ○ | ○ |
| | 7 | DT-2 (0.05) IMTM (0.02) | DMMD (0.12) | DBTDC ($1.2 \times 10^{-4}$) | 1.68/36 | colorless, transparent | 120 | ○ | ○ |
| | 8 | DT-2 (0.04) IMTM (0.04) | KSD (0.12) | DBTDC ($1.2 \times 10^{-4}$) | 1.69/35 | colorless, transparent | 96 | ○ | ○ |
| | 9 | DT-2 (0.06) | MES (0.12) | DMTDC ($1.2 \times 10^{-4}$) | 1.66/38 | colorless, transparent | 119 | ○ | ○ |
| | 10 | DT-2 (0.06) | KSD (0.12) | DBTDL ($1.2 \times 10^{-4}$) | 1.68/36 | colorless, transparent | 108 | ○ | ○ |
| | 11 | DT-3 (0.03) DIITP (0.02) | KSD (0.12) | DMTDC ($1.2 \times 10^{-4}$) | 1.68/37 | colorless, transparent | 106 | ○ | ○ |
| Application Comparative Example | 1 | XDI (0.12) | PETMP (0.06) | DBTDL ($1.2 \times 10^{-4}$) | 1.59/35 | colorless, transparent | 86 | Δ | ○ |
| | 2 | TDI (0.12) | XDT (0.07) PETMA (0.025) | DBTDL ($1.2 \times 10^{-4}$) | 1.68/25 | yellow | 128 | X | X |
| | 3 | IES (0.12) | TMM (0.06) | DBTDL ($1.2 \times 10^{-4}$) | 1.66/33 | colorless, transparent | 71 | ○ | X |

Note:
DT-1: 2,5-bis(4-isocyanato-2-thiabutyl)-1,4-dithian,
DT-2: 2,5-bis(3-isocyanatomethyl-4-isocyanato-2-thiabutyl)-1,4-dithian,
DT-3: 2,5-bis(3-isocyanato-2-thiapropyl)-1,4-dithian,
CHTI: 1,3,5-triisocyanatocyclohexane,
HMTI: 1,3,5-tris(isocyanatomethyl)cyclohexane,
IMTM: bis(isocyanatomethylthio)methane,
DIITP: 1,5-diisocyanato-2-isocyanatomethyl-3-thiapentane,
DMMD: 2,5-bis(mercaptomethyl)-1,4-dithian,
PETMP: pentaerythritol tetrakis(3-mercaptopropionate),
KSD: 2,5-bis(mercaptomethyl)-1,4-dithian-dimer,
TMP: 1,2,3-trimercaptopropane,
MES: 2-mercaptoethyl sulfide,
DBTDL: di-n-butyltin dilaurate,
DMTDC: di-methyltin dichloride,
DBTDC: di-n-butyltin dichloride,
XDI: m-xylene diisocyanate,
TDI: tolylene diisocyanate,
IES: 2-isocyanatoethyl sulfide,
XDT: m-xylene dithiol,
PETMA: pentaerythritol tetrakis(2-mercaptoacetate),
TMM: tetrakis(4-mercapto-2-thiabutyl)methane

The invention provides a polyisocyanate compound having a 1,4-dithian ring in the main skeleton and the sulfur atom in the side chain, in which the refractive index and the Abbe number are high. It has from 2 to 4 isocyanate groups, is easily polymerized with at least one type of a compound having two or more hydroxyl groups in a molecule, a compound having two or more mercapto groups in a molecule and a compound having one or more hydroxyl groups and one or more mercapto groups in a molecule to provide an optical material. Since the optical material obtained by using the polyisocyanate compound has the 1,4-dithian ring contributing to the heat resistance and further the sulfur atom in the basic skeleton, the refractive index and the Abbe number are high, the heat resistance, the weatherability and the transparency are excellent, and no optical distortion is observed. The optical material is preferably used in lenses such as a spectacle lens, a camera lens and the like, a prism, optical fibers, substrates for recording medium used in an optical disk, a magnetic disk and the like, and optical products such as a filter and the like. It can also be used in ornamental products such as glasses, vases and the like which are obtained by making the most of the property of the high refractive index.

Since the optical material of the invention has the 1,4-dithian ring contributing to the heat resistance and, in addition to this, a sulfur atom in the basic skeleton, the refractive index and the Abbe number are high. In addition, the heat resistance, the weatherability and the transparency are excellent and no optical distortion is observed. The optical material is preferably used in lenses such as spectacle lenses, a camera lenses and the like, prisms, optical fibers, in a substrate for a recording medium used in an optical disk, a magnetic disk and the like, a filter and the like. It can also be used in ornamental products such as glass, vases and the like, taking advantage of the high refractive index.

The descriptions presented herein enable a person of ordinary skill in the art to make and use the invention. Although the invention has been fully described by way of examples with reference to the accompanying drawings, it is to be noted that various modifications will be readily apparent to those skilled in the art, and the generic principles defined herein may be applied to other embodiments and applications without departing from the spirit and scope of the invention. Thus, the invention is not intended to be limited to the embodiments shown, but is to be accorded the widest scope consistent with the principles and features disclosed herein.

What is claimed is:

1. An optical material obtained by reacting a mixture comprising: component (A) comprising a polyisocyanate compound represented by general formula (I)

wherein m and n independently represent an integer from 1 to 3 and wherein X and Y independently represent a first alkylene group having from 1 to 5 carbon atoms or a second alkylene group having from 1 to 5 carbon atoms to which an isocyanatoalkyl group is bound, wherein the carbon number of the alkyl group of the isocyanatoalkyl group is between 1 and 3, said first or second alkylene group optionally having a sulfur atom, and component (B) comprising at least one compound selected from the group consisting of (i) a compound having two or more mercapto groups in a molecule, (ii) a compound having two or more hydroxyl groups in a molecule and (iii) a compound having one or more hydroxyl groups and one or more mercapto groups in a molecule.

2. The optical material of claim 1, wherein said X and said Y are each a methylene group or an ethylene group.

3. The optical material recited in claim 1, wherein said X and said Y are each a methylene group having a bound isocyanatomethyl group, an ethylene group having an isocyanatomethyl group bound to a carbon atom bound to a sulfur atom or an ethylene group having an isocyanatomethyl group bound to a carbon atom bound to an isocyanate group.

4. The optical material of claim 1, 2, or 3, wherein m and n are both 1.

5. The optical material of claim 1, 2 or 3, wherein the compound having two or more mercapto groups in the molecule is a compound represented by general formula (II-a)

wherein a represents an integer from 1 to 20.

6. An optical product formed of the optical material of claim 1, 2, or 3.

7. An optical material formed of a poly(thio)urethane obtained by subjecting the mixture of claim 1 to a polyaddition reaction.

* * * * *